United States Patent [19]

Fowler et al.

[11] Patent Number: 5,720,961
[45] Date of Patent: Feb. 24, 1998

[54] SKIN CLEANSING COMPOSITIONS

[75] Inventors: Timothy John Fowler, Cincinnati; Richard Loren McManus, West Chester; George Endel Deckner, Cincinnati, all of Ohio

[73] Assignee: The Procter & Gamble Company, Cincinnati, Ohio

[21] Appl. No.: 521,287

[22] Filed: Aug. 29, 1995

Related U.S. Application Data

[63] Continuation of Ser. No. 296,565, Aug. 26, 1994, abandoned.

[51] Int. Cl.$^6$ .............................. A61K 9/10; A61K 9/14; A61K 7/02

[52] U.S. Cl. .................. 424/401; 424/489; 424/70.19; 424/70.21; 424/78.02; 514/844; 514/846; 514/937; 514/873; 514/952; 514/975

[58] Field of Search ....................... 424/401, 489, 424/70.19, 70.21, 78.02; 514/844, 846, 937

[56] References Cited

U.S. PATENT DOCUMENTS

| | | | |
|---|---|---|---|
| 3,383,280 | 5/1968 | Kuehns | 167/58 |
| 3,645,904 | 2/1972 | Beach | 252/89 |
| 3,819,525 | 6/1974 | Hattenbrun | 252/132 |
| 3,839,213 | 10/1974 | Hill | 252/89 |
| 3,944,506 | 3/1976 | Hramchenko et al. | 252/526 |
| 4,164,563 | 8/1979 | Chang | 424/83 |
| 4,309,411 | 1/1982 | Toida et al. | 424/63 |
| 4,508,634 | 4/1985 | Elepano et al. | 252/163 |
| 4,537,604 | 8/1985 | Dawson | 51/298 |
| 4,557,853 | 12/1985 | Collins | 252/128 |
| 4,673,526 | 6/1987 | Zabotto et al. | 252/174.16 |
| 4,992,476 | 2/1991 | Geria | 514/782 |
| 5,135,740 | 8/1992 | Katz et al. | 424/401 |
| 5,154,849 | 10/1992 | Visscher et al. | 252/174.15 |
| 5,385,729 | 1/1995 | Prencipe et al. | 424/70.11 |

FOREIGN PATENT DOCUMENTS

| | | | |
|---|---|---|---|
| 1059554 | 3/1982 | China | C11D 1/79 |
| 0 105 657 | 4/1984 | European Pat. Off. | A61K 7/48 |
| 0 257 458 | 8/1987 | European Pat. Off. | A61K 7/50 |
| 0 295 886 | 6/1988 | European Pat. Off. | A61K 7/02 |
| 0 412 865 | 2/1991 | European Pat. Off. | A61K 7/00 |
| 0 571 193 | 5/1993 | European Pat. Off. | A61K 7/48 |
| 2563104 | 10/1985 | France | A61K 7/48 |
| 2437165 | 1/1976 | Germany | A61K 7/48 |
| 2758202 | 7/1979 | Germany | C11D 3/12 |
| 3736970 | 5/1989 | Germany | A61K 7/50 |
| 51-121530 | 10/1976 | Japan | A61K 7/00 |
| 58-192814 | 11/1983 | Japan | A61K 7/00 |
| 61-171415 | 8/1986 | Japan | A61K 7/00 |
| 63-212462 | 9/1988 | Japan | A61K 7/16 |
| 63-238008 | 10/1988 | Japan | A61K 7/00 |
| 63-295504 | 12/1988 | Japan | A61K 7/00 |
| 03106809 | 5/1991 | Japan | A61K 7/00 |
| 04154717 | 5/1992 | Japan | A61K 7/50 |
| 04359999 | 12/1992 | Japan | C11D 9/60 |
| 05221822 | 8/1993 | Japan | A61K 7/00 |
| 06072827 | 3/1994 | Japan | A61K 7/50 |
| 1 288 805 | 9/1969 | United Kingdom | C11D 1/12 |
| 1 319 413 | 12/1970 | United Kingdom | A61K 7/00 |

OTHER PUBLICATIONS

Micronized Waxes for the Printing Ink, Paint and Coatings Industries, Micro Powders, Inc., Tarrytown, NY, Mar. 1993.

A–C Performance Additives, Allied–Signal Inc., 1990.

Material Data Safety Sheet, Fine Particle Size Oxidized Polyethylene Homopolymers, Allied–Signal Inc., Dec. 1992.

*Primary Examiner*—Thurman K. Page
*Assistant Examiner*—James M. Spear
*Attorney, Agent, or Firm*—Anthony D. Sabatelli; David K. Dabbiere

[57] ABSTRACT

The present invention relates to non-abrasive personal care cleansing compositions. These compositions utilize insoluble micronized cleansing particles of defined particle size that are not tactilely perceived by the user during the cleansing process, and yet which provide improved cleansing performance from the composition. These compositions also comprise a surfactant, an emollient and water.

2 Claims, No Drawings

SKIN CLEANSING COMPOSITIONS

This is a continuation of application Ser. No. 08/296,565, filed on Aug. 26, 1994, now abandoned.

TECHNICAL FIELD

The present invention relates to personal care compositions useful for cleansing the skin and hair. These compositions contain insoluble micronized cleansing particles in a cleansing base. These particles are chosen to provide a cleansing benefit, yet without being tactilely detectable or unduly causing abrasion.

BACKGROUND OF THE INVENTION

Personal cleansing compositions must satisfy a number of criteria to be acceptable to consumers. These criteria include cleansing power, skin feel, mildness to the skin, hair, and occular mucosae, and often in the case of surfactant-based cleansers, lather volume. Ideal personal cleansers should gently cleanse the skin or hair, causing little or no irritation and without leaving the skin overly dry or taut after frequent use.

One approach to personal cleansing is to utilize surfactants to aid in the removal of dirt, oil, and debris (e.g., make-up). However, with surfactant-based cleansing systems, a trade-off exists between mildness and cleansing and lathering ability. The most effective cleansing and lathering surfactants tend to be the harshest and most irritating. On the other hand, surfactants that are known to be mild tend to have the drawback of poor cleansing and lather performance compared to the highest bar soap standards (e.g., coconut soaps). One solution to this problem has been to attempt to find a middle ground by balancing the surfactant system for mildness and cleansing and lathering ability.

Another approach to personal cleansing is to utilize solvents and emollients to aid in the removal of dirt, oil, and debris. Even though solvents and emollients are effective cleansers, these materials have the disadvantage of being more difficult to remove by rinsing and of tending to leave the skin with a coated, greasy feel. Also, most solvents and emollients have low water solubility which means that they must either be used in an anhydrous system or formulated with a high solvent level to provide effective cleansing.

Yet another approach to personal cleansing is to rely on the physical abrasion of suspended particles to remove oil, dirt, and other debris. A wide variety of cleansing compositions containing abrasive particles are known in the marketplace, but these compositions suffer from the disadvantage of giving an unpleasant sensation of scratchiness to the user, or even worse, of actually damaging the skin by abrading it. In fact many abrasive scrub products are perceived as too harsh and irritating for everyday use.

Therefore, it is seen that conventional surfactant based cleansers, emollient and solvent cleansers, and cleansers utilizing abrasive particles all suffer from disadvantages. Clearly, a need exists to develop personal cleansing compositions which provide effective skin cleansing benefits without the disadvantages of harsh surfactants, heavy emollients and solvents, and overly abrasive particles.

It has been surprisingly found in the present invention that highly efficacious cleansing compositions can be prepared which utilize certain small diameter micronized particles to achieve improved cleansing efficacy. In these compositions the particles are of such a size as to be below the tactile perception threshold of the user (i.e. the particles cannot be felt during the cleansing process). Without being limited by theory, it is believed that these small particles are still large enough to physically boost the cleansing power of mild surfactant or emollient and solvent systems by lifting away dirt, oil, and other debris. It has been found herein that particles having a mean particle size diameter from about 1 micron to about 75 microns are most useful for this purpose and permit the formulation of non-abrasive, non-irritating cleansing products, which are ideal for daily use. It has also been found that particular attention must be given to ensuring that the particles employed do not have a significant percentage of particles above about 75 microns.

It is therefore an object of the present invention to provide personal cleansing compositions useful for cleansing the skin and hair.

It is another object of the present invention to provide personal cleansing compositions utilizing micronized particles such that the compositions have good cleansing ability without irritating or abrading the skin.

It is another object of the present invention to provide personal cleansing compositions utilizing micronized particles in combination with mild surfactant systems.

It is another object of the present invention to provide personal cleansing compositions utilizing micronized particles in combination with mild surfactant systems and emollients and solvents.

It is another object of the present invention to provide a method for cleansing the skin or hair.

These and other objects of this invention will become apparent in light of the following disclosure.

SUMMARY OF THE INVENTION

The present invention relates to a nonabrasive personal cleansing composition comprising:

(a) from about 0.1% to about 20% of insoluble particles having a is mean particle size diameter from about 1 micron to about 75 microns, with greater than about 95% of said particles in said composition having a diameter less than about 75 microns, (b) from about 0.05% to about 40% of a surfactant selected from the group consisting of nonionic surfactants, anionic surfactants, cationic surfactants, amphoteric surfactants, zwitterionic surfactants, and mixtures thereof, (c) from 0% to about 50% of an emollient, and (d) from about 20% to about 99.85% water.

All percentages and ratios used herein are by weight of the total composition and all measurements made are at 25° C., unless otherwise designated. All weight percentages, unless otherwise indicated, are on an actives weight basis. The invention hereof can comprise, consist of, or consist essentially of, the essential as well as optional ingredients and components described herein.

DETAILED DESCRIPTION OF THE INVENTION

The personal cleansing compositions of the present invention are highly efficacicious for cleansing the skin or hair without being irritating or abrasive or leaving the skin feeling greasy or coated. These cleansers can be prepared in a wide variety of forms including liquids, emulsions, cold creams, gels, bars, and the like, and can also be delivered from bottles, tubes, pumps, squeeze foamers, and aerosol containers as foams, mousses, and lathers.

The term "micronized", as used herein, means that the particles have a mean particle size diameter within about two orders of magnitude of a micron. In other words, the term as used herein, means that the particles can be defined in micron units without having to resort to unduly large or small exponential values.

The term "nonabrasive", as used herein, means that the compositions of the present invention do not have an abrasive or scratchy feel that is perceptible to the user.

The term "topical application", as used herein, means to apply or spread the compositions of the present invention to the surface of the skin or scalp and hair.

The term "pharmaceutically-acceptable", as used herein, means that the compositions or components thereof so described are suitable for use in contact with human tissue without undue toxicity, incompatibility, instability, allergic response, and the like.

INSOLUBLE MICRONIZED PARTICLES

The compositions of the present invention comprise from about 0.1% to about 20%, more preferably from about 0.5% to about 15%, and most preferably from about 2.5% to about 10% of insoluble micronized particles, based on the weight of the total composition.

The term "insoluble", as used herein, means that the particles are essentially insoluble in the compositions of the present invention. In particular, the insoluble particles should have a solubility less than about 1 gram per 100 grams of composition at 25° C., preferably less than about 0.5 grams per 100 grams of composition at 25° C.; and more preferably less than about 0.1 grams per 100 grams of composition at 25° C.

These micronized particles have a mean particle size diameter and particle size distribution such that they are below the tactile perception threshold of most users, and yet are not so small as to be ineffective for aiding in oil, dirt, and debris (e.g., make-up) removal. It is found herein that particles having a mean particle size diameter greater than about 75 microns are tactilely perceived during the cleansing process and it is important to minimize the amount of these larger particles in the compositions. Conversely, it is found that particles having a mean particle size diameter of less than about 1 to about 5 microns are generally less effective for providing a cleansing benefit. Without being limited by theory, it is believed that the insoluble cleansing particles should be of a size that is on the order of the thickness of the dirt, oil, or debris layer to be cleaned away. This layer is believed to be on the order of a few microns in thickness in most instances. Most conventional abrasive cleansers utilize particles typically having a particle size diameter in the 150–300 micron range, which is far larger than necessary for effective cleansing. Consequently, such products have the disadvantage of having an abrasive feel without necessarily improving cleansing performance beyond that achieved in the present invention. It is therefore found in the present invention that the micronized particles should have a mean particle size diameter from about 1 to about 75 microns, more preferably from about 15 to about 60 microns, and most preferably from about 20 to about 50 microns, so as to provide effective cleansing without being tactilely perceptible.

Additionally, it is also recognized that mean particle size is not the only consideration that is important in determining the suitability of a particle for use herein. For example, even though a particle sample might have the "correct" average particle size diameter, the particle distribution should be such as to have a minimum percentage of the particles above the tactile threshold of above 75 microns. Therefore, the insoluble micronized particles of the present invention also have a particle size distribution such that greater than about 95% of the particles when formulated into the compositions have a particle size less than about 75 microns, preferably greater than about 97.5% of the particles have a particle size less than about 75 microns, more preferably greater than about 99% of the particles have a particle size less than about 75 microns, and most preferably greater than about 99.5% of the particles have a particle size less than about 75 microns.

The particle size of the micronized particles of the present invention can be measured using a variety of different techniques well-known to the formulation scientist of ordinary skill in the art, e.g. laser diffraction, microscopy, filtration, sedimentation, etc. In the present invention, a preferred method of determining particle size is the laser diffraction technique using a commericially available laser particle size analyzer. In the present invention the particle size measurements are determined using a Munhall Particle Size Analyser, Model PSA-32 (available from Munhall Corp.). A variety of solvents of various viscosity and polarity can be used to disperse the particles in the samples to be analyzed for size. Preferred solvents include water, hexanes, and isoproponal, with isopropanol being more preferred.

Particles having a wide range of shapes, surface characteristics, and hardness characteristics can be utilized herein provided the particle size requirements are met.

The water-insoluble, micronized particles of the present invention can be derived from a wide variety of materials including those derived from inorganic, organic, natural, and synthetic sources. Nonlimiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magneisum trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e. polytetrafluoroethylene), polyhalogenated olefins, pumice rice bran, rye flour, sericite, silica, silk, sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like. Typically, the polymeric and mixed polymeric particles are treated via an oxidation process to destroy impurities and the like. The polymeric and mixed polymeric particles can also optionally be crosslinked with a variety of common crosslinking agents, nonlimiting examples of which include butadiene, divinyl benzene, methylenebisacrylamide, allyl ethers of suscrose, allyl ethers of pentaerythritol, and mixtures thereof. Other examples of useful micronized particles include waxes and resins such as paraffins, carnuba wax, ozekerite wax, candellila wax, urea-formaldehyde resins, and the like. When such waxes and resins are used herein it is important that these materials are solids at ambient and skin temperatures.

Among the preferred water-insoluble, micronized particulate materials useful herein are the synthetic polymeric particles selected from the group consisting of polybutylene, polyethylene, polyisobutylene, polymethylstyrene, polypropylene, polystyrene, polyurethane, nylon, teflon, and mixtures thereof.

Most preferred are polyethylene and polypropylene micronized particles, with the oxidized versions of these materials being especially preferred. Examples of commercially available particles useful herein include the ACumist™ micronized polyethylene waxes available from Allied Signal (Morristown, N.J.) available as the A, B, C, and D series in a variety of average particle sizes ranging from 5 microns to 60 microns. Preferred are the ACumist™ A-25, A-30, and A-45 oxidized polyethylene particles having a mean particle size diameter of 25, 30, and 45 microns, respectively. Examples of commercially available polypropylene particles include the Propyltex series available from Micro Powders (Dartek).

SURFACTANTS

The compositions of the present invention comprise from about 0.05% to about 40%, preferably from about 0.10% to about 20%, more preferably from about 0.5% to about 15%, and most preferably from about 1% to about 10% of a surfactant selected from the group consisting of nonionic surfactants, anionic surfactants, cationic surfactants, amphoteric surfactants, zwitterionic surfactants, and mixtures thereof. In further embodiments, wherein the compositions of the present invention are in the form of soap bars, it is found to be highly advantageous to utilize higher levels of surfactants, i.e. from about 50% to about 90%.

Suitable surfactants for use in the compositions of the present invention are disclosed in McCutcheon's, *Detergents and Emulsifiers*, North American edition (1986), published by allured Publishing Corporation; U.S. Pat. No. 5,151,210, to Steuri et al., issued Sep. 29, 1992; U.S. Pat. No. 5,151,209, to McCall et al., issued Sep. 29, 1992; U.S. Pat. No. 5,120,532, to Wells et al., issued Jun. 9, 1992; U.S. Pat. No. 5,011,681, to Ciotti et al., issued Apr. 30, 1991; U.S. Pat. No. 4,788,006, to Bolich, Jr. et al., issued Nov. 29, 1989; U.S. Pat. No. 4,741,855, to Grote et al, issued May 3, 1988; U.S. Pat. No. 4,704,272, to Oh et al, issued Nov. 3, 1987; U.S. Pat. No. 4,557, 853, to Collins, issued Dec. 10, 1985; U.S. Pat. No. 4,421,769, to Dixon et al., issued Dec. 20, 1983; and U.S. Pat. No. 3,755,560, to Dickert et al., issued Aug. 28, 1973; each of these documents being incorporated herein by reference in its entirety. It is to be understood that even though the term surfactant is used herein in this section to describe these materials, that the term is not meant to exclude materials which also have emulsification properties, as it is well known to one skilled in the art that a surfactant can also have emulsification properties and vice versa.

Among the nonionic surfactants that are useful herein are those that can be broadly defined as condensation products of long chain alcohols, e.g. C8–30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel).

Other useful nonionic surfactants include the condensation products of alkylene oxides with fatty acids (i.e. alkylene oxide esters of fatty acids). These materials have the general formula $RCO(X)_n OH$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_n OOCR$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)_n OR'$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_n OR'$ wherein R and R' are C10–30 alkyl groups, X is —OCH$_2$CH$_2$ (i.e. derived from ethylene glycol or oxide) or —OCH$_2$CHCH$_3$— (derived from propylene glycol or oxide), and n is an integer from about 1 to about 100. Nonlimiting examples of these alkylene oxide derived nonionic surfactants include ceteth-1, ceteth-2, ceteth-6, ceteth-10, ceteth-12, ceteraeth-2, ceteareth-6, ceteareth-10, ceteareth-12, steareth-1, steareth-2, stearteth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

A wide variety of anionic surfactants are useful herein. See, e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO$—$OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof. Preferred for used herein are ammonium cocoyl isethionate, sodium cocoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1\text{---}SO_3\text{---}M$$

wherein $R_1$ is chosen from the group consisting of a straight or branched chain, saturated aliphatic hydrocarbon radical having from about 8 to about 24, preferably about 12 to about 18, carbon atoms; and M is a cation. Still other anionic synthetic surfactants include the class designated as succinamates, olefin sulfonates having about 12 to about 24 carbon atoms, and b-alkyloxy alkane sulfonates. Especially preferred sulfates for use herein include sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Nonlimiting examples of cationic surfactants useful herein include cationic ammonium salts such as those having the formula:

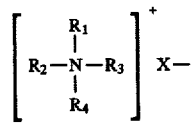

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group ranging from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ alternatively $R_5CO$—$(CH_2)_n$—; wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a cocunt fatty acid, which generally have mixtures of alkyl chains in the C12 to C14 range. Examples of quaternary ammonium salts derived from these tallow and cococut sources include ditallow dimethyl ammonium chlroide, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred cationic surfactants are those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Most preferred cationic surfactants are those selected from the group consisting of dilauryl dimethyl ammoniun chloride, distearyl dimethyl ammonium chloride, dimyristyl dimethyl ammonium chloride, dipalmityl dimethyl ammonium chloride, distearyl dimethyl ammonium chloride, and mixtures thereof.

Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivates. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Especially useful herein as amphoteric or zwitterionic surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other highly useful amphoteric and zwitterionic surfactants include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Among the surfactants described above, preferred for use herein are those selected from the group consisting of sodium cetearyl sulfate, sodium lauryl sulfate, sodium lauryl sarcosinate, sodium cocoyl isethionate, coamidopropyl betaine, sodium laureth sulfate, cetyl dimethyl betaine, ammonium lauryl sulfate, sodium tallow soap, sodium coconut soap, ceteth-10, steareth-21, steareth-2, ceteth-2, glyceryl stearate, glucose amides, dilauryl dimethyl ammonium chloride, distearyl dimethyl ammonium chloride, dimyristyl dimethyl ammonium chloride, dipalmityl dimethyl ammonium chloride, and mixtures thereof.

EMOLLIENTS

The compositions of the present invention comprise from 0% to about 50%, preferably from about 0.1% to about 20%, and most preferably from about 0.5% to about 10% of an emollient. Without being limited by theory, it is believed that these emollient materials provide a cleansing benefit by acting as a solvent to help dissolve oils and other oily debris during the cleansing process. The term emollient, as used herein is intended to include conventional lipid materials (e.g., fats, waxes, and other water insoluble materials), polar lipids (e.g., lipid materials which have been hydrophylically modified to render them more water soluble), silicones, hydrocarbons, and a wide variety of solvent materials.

A wide variety of emollient materials are suitable for use in the compositions of the present invention. Examples of conventional emollients include C8–30 alkyl esters of C8–30 carboxylic acids; C1–6 diol monoesters and diesters of C8–30 carboxylic acids; monoglycerides, diglycerides, and triglycerides of C8–30 carboxylic acids, cholesterol esters of C8–30 carboxylic acids, cholesterol, and hydrocarbons. Examples of these materials include diisopropyl adipate, isopropyl myristate, isopropyl palmitate, ethylhexyl palmitate, isodecyl neopentanoate, C12–15 alcohols benzoate, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters, mineral oil, petrolatum, and straight and branched hydrocarbons having from about 16 to about 30 carbon atoms. Also useful are straight and branched chain alcohols having from about 10 to about 30 carbon atoms, nonlimiting examples of which include stearyl alcohol, isostearyl alcohol, behenyl alcohol, cetyl alcohol, isocetyl alcohol, and mixtures thereof.

Examples of other suitable materials are disclosed in U.S. Pat. No. 4,919,934, to Deckner et al., issued Apr. 24, 1990; which is incorporated herein by reference in its entirety.

Also useful as emollients are material such as alkoxylated ethers and diethers. The alkoxylated ethers useful herein can be described by the following general formula:

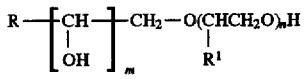

wherein R is selected from the group consisting of H and C1–C30 straight chain or branched chain alkyl, m is an integer from 0 to about 6, R' is selected from the group consisting of methyl and ethyl, and n is an integer from about 3 to about 30.

Preferably R is selected from the group consisting of C2–C25 straight chain or branched alkyl, m is an integer from 0 to about 2, R' is methyl, and n is an integer from about 5 to about 25. More preferably R is selected from the group consisting of C2–C20 straight chain or branched chain alkyl, m is an integer from 0 to about 1, R' is methyl, and n is an integer from about 10 to about 20.

Nonlimiting examples of alkoxylated ethers useful herein include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof. Most preferred are PPG-14 butyl ether (available as Fluid AP from Union Carbid Corp.) and PPG-15 stearyl ether (available under the tradename Arlamol E from ICI Americas Corporation).

Also useful herein are alkoxylated diethers. These compounds can be represented by the general formula:

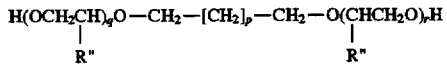

wherein each R" is selected from the group consisting of methyl and ethyl, p is an integer from about 1 to about 6, and each q and r are independently selected so that their sum is an integer from about 3 to about 30. Preferably R" is methyl, p is an integer from about 2 to about 4, and each q and r are independently selected so that their sum is an integer from about 5 to about 25. More preferably R" is methyl, p is an integer from 2 to about 4, and each q and r are independently selected so that their sum is an integer from about 10 to about 20.

Nonlimiting examples of alkoxylated diethers useful herein include those selected from the group consisting of PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof. More preferred is PPG-10 1,4-butanediol diether. This compound is commercially available under the tradename Macol 57 from PPG/Mazer Corporation.

Also useful as emollients are the so-called "polar lipids" which contain hydrophilic moieties such as hydroxy groups carbonyl groups and ether linkages. Preferred classes of these polar lipids include C10–20 alcohol monosorbitan esters, C10–20 alcohol sorbitan diesters, C10–20 alcohol sorbitan triesters, C10–20 alcohol sucrose monoesters, C10–20 alcohol sucrose diesters, C10–20 alcohol sucrose triesters, and C10–20 fatty alcohol esters of C2–C6 2-hydroxy acids. Nonlimiting examples of these polar lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan sesquistearte, sorbitan stearate, sorbitan triiostearte, sorbitan trioleate, sorbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof. Other polar lipids are the C10–20 alkyl pidolates (i.e. pyrrolidone carboxylate esters, examples of which are myristyl pidolate, cetyl pidolate, lauryl pidolate, and stearyl pidolate). Yet other polar lipids are alkyl C1–3 esters of panthenol such as panthenyl triacetate (which is the triacetyl ester of panthenol). Especially preferred among the polar lipids are isostearyl lactate (available as Pationic IL, from RITA Corp), sorbitan laurate (available as Arlacel 20 from ICI Americas), lauryl pyrrolidone carboxylic acid (available as lauryl pidolate from UCIB Corp.), panthenyl triacetate (available as D-panthenyl triacetate from Induchem), and mixtures thereof.

Also useful are silicones including nonvolatile silicones such as dimethicone copolyol; dimethylpolysiloxane; diethylpolysiloxane; high molecular weight dimethicone (average molecular weight from about 200,000 to about 1,000,000 and, preferably, from about 300,000 to about 600,000) which can have various end-terminating groups such as hydroxyl, lower C1–$C_3$ alkyl, lower C1–$C_3$ alkoxy and the like; mixed $C_1$ –$C_3$ alkyl polysiloxane (e.g., methylethylpolysiloxane); phenyl dimethicone and other aryl dimethicones; dimethiconol; fluorosilicones; and mixtures thereof.

Preferred among the nonvolatile silicones are those selected from the group consisting of dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Especially preferred is dimethiconol which is a dimethyl silicone polymer terminated with hydroxyl groups. Dimethiconol is available as Q2-1401 Fluid, a solution of 13 percent ultra-high-viscosity dimethiconol in volatile cyclomethicone fluid as a carrier; as Q2-1403 Fluid, a solution of ultra-high-viscosity dimethiconol fluid in dimethicone (both sold by Dow Corning Corporation); and as other custom blends (e.g. 10% dimethiconol in dimethicone). Nonlimiting examples of silicones useful herein are described in U.S. Pat. No. 5,011,681, to Ciotti et al., issued Apr. 30, 1991, which has already been incorporated by reference.

Among the emollients preferred are those selected from the group consisting of mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearte, sorbitan dilaurate, sorbitan stearate, sorbitan laurate, sucrose laurate, sucrose dilaurate, sodium isostearyl lactylate, lauryl pidolate, sorbitan stearate, stearyl acohol, cetyl alcohol, behenyl alcohol, PPG-14 butyl ether, PPG-15 stearyl ether, and mixtures thereof.

Water

The compositions of the present invention comprise from about 20% to about 99.85%, more preferably from about 50% to about 95%, and most preferably from about 70% to about 90% of water. In further embodiments wherein the compositions of the present invention are in the form of soap bars, lower levels of water are preferred, i.e. from about 5% to about 20%.

Additional Components

The compositions of the present invention can comprise a wide range of additional components. The CTFA Cosmetic Ingredient Handbook, Second Edition, 1992, which is incorporated by reference herein in its entirety, describes a wide variety of nonlimiting cosmetic and pharamceutical ingredients commonly used in the skin care industry, which are suitable for use in the compositions of the present invention. Nonlimiting examples of functional classes of ingredients are described at page 537 of this reference. Examples of these functional classes include: absorbents, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, skin-conditioning agents (humectants, miscellaneous, and occulsive), sunscreen agents, and ultraviolet light absorbers. Examples of other functional classes of materials useful herein that are well known to one of ordinary skill in the art include emulsifiers, solubilizing agents, sequestrants, keratolytics, retinoids, and the like.

Nonlimiting examples of these additional components cited in the CTFA Cosmetic Ingredient Handbook, as well as other materials useful herein, include the following: vitamins and derivatives thereof (e.g. tocopherol, tocopherol acetate, retinoic acid, retinol, retinoids, and the like); sunscreening agents; anti-oxidants; anti-microbial agents; preservatives; thickeners (e.g. crosslinked acrylic acid hompolymers such as the Carbomer series and the acrylates/C10-30 alkyl acrylate crosspolymers available as the Pemulen series from B.F. Goodrich; nonionic polyacrylamide polymers such as the material given the CTFA designation polyacrylamide and isoparaffin and laueth-7 available as Sepigel 305 from Seppic Corporation, Fairfield, N.J.; and crosslinked cationic polymers such as the material given the CTFA designation polyqauaternium 32 (and) mineral and sold as Salcare SC92 and the material given the CTFA designation polyquaternium 37 (and) mineral oil (and) PPG-1 trideceth-6 and sold as Salcare SC95, both by Allied Colloids, Norfolk, Va.); gums (e.g., xanthan gum guar gum gellan gum an the like); emulsifiers; polyethyleneglycols and polypropyleneglyocls; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; anti-acne medicaments (e.g., resorcinol, sulfur, salicylic acid, erythromycin, zinc, benzoyl peroxide, and the like); skin bleaching (or lightening) agents including but not limited to hydroquinone, kojic acid; antioxidants; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabolol, dipotassium glycyrrhizinate and the like; and skin conditioning agents such as urea and glycerol, and also the propoxylated glycerols described in U.S. Pat. No. 4,976,953, to Orr et al., issued Dec. 11, 1990, which is incorporated by reference herein in its entirety. Preferred levels of skin conditioning agents such as glycerol, urea, and propoxylated glycerols range from about 0.1% to about 10%.

In a preferred composition of the present invention, the compositions comprise from about 0.1% to about 10% of a material selected from the group consisting of salicylic acid, glycolic acid, lactic acid, retinal, retinoic acid, azaleic acid, aloe vera, panthenol, pantothenic acid, clove oil, menthol, camphor, eucalyptus oil, eugenol, menthyl lactate, witch hazel distillate, allantoin, bisabolol, and mixtures thereof.

Methods For Personal Cleansing

The compositions of the present invention are useful for cleansing the skin or hair. Typically, a suitable or effective amount of the cleansing composition is applied to the skin or hair to be cleansed. Alternatively, a suitable amount of the cleansing composition can be applied via intermediate application to a washcloth, a sponge, pad, cotton ball or other application device. If desired the area to be cleansed can be premoistened with water. It has been found that the compositions of the present invention can be combined with water during the cleansing process or used alone. The product can be removed after use either by rinsing the product with water, or simply wiping off the product with a tissue, cotton ball, etc. Generally an effective amount of product to be used will depend upon the needs and usage habits of the individual. Because these compositions are essentially non-abrasive, they can be used frequently such as on a daily basis or more than once a day for each cleansing, without undue irritation. Typical amounts of the present compositions useful for cleansing range from about 0.5 mg/cm$^2$ to about 25 mg/cm$^2$ of skin surface area to be cleansed.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

Emollient Cleanser

A cleanser is prepared by combining the following ingredients using conventional mixing techniques.

| Ingredients | Weight Percent |
| --- | --- |
| Water | QS 100 |
| PPG-14 Butyl Ether | 3.25 |
| Glycerin | 3.00 |
| Stearyl Alcohol | 2.88 |
| Polyethylene Particles[1] | 2.00 |
| Polyethylene Particles[2] | 2.00 |
| Salicylic Acid | 2.00 |
| Distearyl Dimethyl Ammmonium Chloride | 1.50 |
| Cetyl Alcohol | 0.80 |
| Urea | 0.50 |
| Steareth-21 | 0.50 |
| Behenyl Alcohol | 0.32 |
| PPG-30 | 0.25 |
| Steareth-2 | 0.25 |
| Fragrance | 0.15 |
| Polysaccharide Gum | 0.05 |
| Disodium EDTA | 0.01 |

[1] Oxidized Polyethylene Particles having a mean particle size diameter of 25 microns, available as Acumist A-25 from Allied Signal Corp.
[2] Oxidized Polyethylene Particles having a mean particle size diameter of 45 microns, available as Acumist A-45 from Allied Signal Corp. Micronized In a suitable vessel the water, glycerin, polysaccharide gum, and disodium EDTA are mixed and heated to 75°–80° C. with stirring. In a separate vessel the PPG-14 butyl ether, the PPG-30, and the salicylic acid are heated to 75°–80° C. with stirring to form an oil phase. Next the stearyl, cetyl, and behenyl aolcohols are added to this oil phase while continuing to heat and stir. Next the distearyl dimethyl ammonium chloride, the steareth-2, and steareth-21, are added to this oil phase while still continuing to heat and stir. This oil phase is then emulsified into the water-containing mixture using a homogenizing mill. The resulting emulsion is cooled with stirring to 45° C. and the urea and fragrance are added. The emulsion is cooled to room temperature with stirring at which time the polyethylene particles are mixed in.

The resulting cleanser exhibits low skin abrasion and is useful for cleansing the skin.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

Example 2

Emollient Cleanser

A cleanser is prepared by combining the following ingredients using conventional mixing techniques.

| Ingredients | Weight Percent |
| --- | --- |
| Water | QS 100 |
| Glycerin | 3.00 |
| Polyethylene Particles[1] | 4.00 |

-continued

| Ingredients | Weight Percent |
| --- | --- |
| Glucose Amides | 2.56 |
| Sorbitan Stearate | 2.00 |
| Cetyl Alcohol | 0.50 |
| Fragrance | 0.50 |
| Phenoxyethanol | 0.40 |
| Polyquaternium-10 | 0.20 |
| Potassium Hydroxide | 0.20 |
| Acrylates/C10–30 Alkyl Acrylate Cross Polymer | 0.20 |
| Methylparaben | 0.10 |
| Stearic Acid | 0.10 |
| Propylparaben | 0.10 |
| Tetrasodium EDTA | 0.10 |

[1] Oxidized Polyethylene Particles having a mean particle size diameter of 45 microns, available as Acumist A-45 from Allied Signal Corp.

In a suitable vessel the water, glycverin, glucose amides, polyquaternium-10, methylparaben, acrylates/C10–30 alkyl acrylates crosspolymer, and tetrasodium EDTA are mixed and heated to 75°–80° C. with stirring. In a separate vessel the sorbitan stearate, stearic acid, propylparaben, and cetyl alcohol are heated to 75°–80° C. with stirring to form an oil phase. This oil phase is then emulsified into the water-containing mixture using a homogenizing mill. Next, the potassium hydroxide is added to neutralize the emulsion which is then cooled with stirring to 45° C., at which time the phenoxyethanol and fragrance are added. The emulsion is cooled to room temperature with stirring at which time the polyethylene particles are mixed in.

The resulting cleanser exhibits low skin abrasion and is useful for cleansing the skin.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

Example 3

Lathering Cleanser

A lathering cleanser is prepared by combining the following ingredients using conventional mixing techniques.

| Ingredients | Weight Percent |
| --- | --- |
| Water | QS 100 |
| Polyethylene Beads[1] | 4.00 |
| Glycerin | 3.00 |
| Sodium Lauryl Sulfate | 3.00 |
| Sodium Cocoyl Isethionate | 2.00 |
| Cocamidopropyl Betaine | 2.00 |
| Polyquaternium-10 | 0.50 |
| Sodium Laureth Sulfate | 0.40 |
| Phenoxyethanol | 0.40 |
| Methylparaben | 0.10 |
| Propylparaben | 0.10 |
| Disodium EDTA | 0.10 |

[1] Oxidized Polyethylene Particles having a mean particle size diameter of 45 microns, available as Acumist A-45 from Allied Signal Corp.

In a suitable vessel the water, glycerin, polyquaternium-10, disodium EDTA, and methylparaben are heated with stirring to 50° C. In a separate vessel the sodium lauryl sulfate, sodium cocoyl isethionate, cocamidopropyl betaine, sodium laureth sulfate, and propyl paraben are heated with stirring to 50° C. and mixed with the water phase ingredients. The mixture is cooled to 45° C. and the phenoxyethanol is mixed in. The mixture is then cooled to room temperature with mixing at which time the polyethylene particles are mixed in.

The resulting lathering cleanser exhibits low skin abrasion and is useful for cleansing the skin. This lathering cleanser can also be delivered from a non-aerosol pump or squeeze foaming device to deliver a lathering foam.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

Example 4

Emollient Cleanser

A cleanser is prepared by combining the following ingredients using conventional mixing techniques.

| Ingredients | Weight Percent |
| --- | --- |
| Water | QS 100 |
| Cetyl Dimethyl Betaine | 2.00 |
| Sodium Alkyl Sulfate | 1.00 |
| PPG-14 Butyl Ether | 3.25 |
| Glycerin | 3.00 |
| Stearyl Alcohol | 2.88 |
| Polyethylene Particles[1] | 2.00 |
| Polyethylene Particles[2] | 2.00 |
| Salicylic Acid | 2.00 |
| Distearyl Dimethyl Ammonium Chloride | 1.50 |
| Cetyl Alcohol | 0.80 |
| Urea | 0.50 |
| Steareth-21 | 0.50 |
| Behenyl Alcohol | 0.32 |
| PPG-30 | 0.25 |
| Steareth-2 | 0.25 |
| Fragrance | 0.15 |
| Polysaccharide Gum | 0.05 |
| Disodium EDTA | 0.01 |

[1]Oxidized Polyethylene Particles having a mean particle size diameter of 25 microns, available as Acumist A-25 from Allied Signal Corp.
[2]Oxidized Polyethylene Particles having a mean particle size diameter of 45 microns, available as Acumist A-45 from Allied Signal Corp.

In a suitable vessel the water, glycerin, and disodium EDTA are mixed and heated to 75°–80° C. with stirring. In a separate vessel the PPG-14 butyl ether, the salicylic acid, and the PPG-30 are heated to 75°–80° C. with stirring to form an oil phase. Next the stearyl alcohol, cetyl alcohol, and the behenyl alcohol are added to this oil phase while continuing to heat with stirring. Next the distearyl dimethyl ammonium chloride, the steareth-2, and steareth-21, are added to the oil phase while still continuing to heat and stir. This oil phase is then emulsified into the water-containing mixture using a homogenizing mill. The resulting emulsion is cooled with stirring to 45° C. and the urea and fragrance are added. The emulsion is cooled to room temperature with stirring at which time the sodium alkyl sulfate and the cetyl dimethyl betaine are mixed in, followed by the polyethylene particles.

The resulting cleanser exhibits low skin abrasion and is useful for cleansing the skin.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

Example 5

Emulsion Cleanser

A cleanser is prepared by combining the following ingredients using conventional mixing techniques.

| Ingredients | Weight Percent |
| --- | --- |
| Water | QS 100 |
| Glycerin | 3.00 |
| Polyethylene Particles[1] | 4.00 |
| PPG-14 Butyl Ether | 7.00 |
| Mineral Oil | 1.40 |
| PPG-30 | 0.25 |
| Stearyl Alcohol | 1.80 |
| Cetyl Alcohol | 0.50 |
| Behenyl Alcohol | 0.20 |
| Steareth-2 | 1.50 |
| Steareth-21 | 0.50 |
| Disodium EDTA | 0.01 |
| Phenoxyethanol | 0.40 |
| Methylparaben | 0.10 |
| Propylparaben | 0.10 |

[1]Oxidized Polyethylene Particles having a mean particle size diameter of 45 microns, available as Acumist A-45 from Allied Signal Corp.

In a suitable vessel the water, glycerin, methylparaben, and disodium EDTA are mixed and heated to 75°–80° C. with stirring. In a separate vessel the PPG-14 butyl ether, PPG-30, propylparaben, and mineral oil are heated to 75°–80° C. with stirring to form an oil phase. Next the stearyl alcohol, cetyl alcohol, and the behenyl alcohol are added to this oil phase while continuing to heat with stirring. Next the steareth-2, and steareth-21, are added to the oil phase while still continuing to heat and stir. This oil phase is then emulsified into the water-containing mixture using a homogenizing mill. The mixture is cooled to 45° C. and the phenoxyethanol is mixed in. The resulting emulsion is cooled to room temperature with stirring at which time the polyethylene particles are stirred in.

The resulting cleanser exhibits low skin abrasion and is useful for cleansing the skin. This cleanser can be used without water to cleanse the skin using a pad, cotton ball, tissue, or the like.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

Example 6

Non-Rinsing Cleansing Milk

A non-rinsing cleansing milk is prepared by combining the following ingredients using conventional mixing techniques.

| Ingredients | Weight Percent |
| --- | --- |
| Water | QS 100 |
| Mineral Oil | 5.00 |
| Polyethylene Beads[1] | 4.00 |
| Isopropyl Palmitate | 3.00 |
| Cetearyl Alcohol | 2.00 |
| PEG-10 Castor Oil | 2.00 |
| Sodium Cetearyl Sulfate | 1.00 |
| Glyceryl Stearate | 0.25 |
| Acrylamide/Sodium Acrylate Copolymer[2] | 0.25 |
| Dimethicone | 0.20 |
| Phenoxyethanol | 0.40 |
| Methylparaben | 0.10 |
| Propylparaben | 0.10 |

[1]Oxidized Polyethylene Particles having a mean particle size diameter of 25 microns, available as Acumist A-25 from Allied Signal Corp.
[2]Available as Hoe S 2793 from Hoechst Celanese.

In a suitable vessel the water, acrylamide/sodium acrylate copolymer, glyceryl stearate, sodium cetearyl sulfate, and methylparaben are mixed and heated to 75°–80° C. with stirring. In a separate vessel the mineral oil, isopropyl palmitate, cetearyl alcohol, PEG-10 castor oil, dimethicone, and propylparaben are heated to 75°–80° C. with stirring to form an oil phase. This oil phase is then emulsified into the water-containing mixture using a homogenizing mill. The mixture is cooled to 45° C. with stirring and the phenoxyethanol is mixed in. The resulting emulsion is cooled to room temperature at which time the polyethylene particles are stirred in.

The resulting cleanser exhibits low skin abrasion and is useful for cleansing the skin. This cleanser can be used without water to cleanse the skin using a pad, cotton ball, tissue, or the like.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

Example 7

Bar Soap

| Ingredients | Weight Percent |
| --- | --- |
| Water | QS 100 |
| Sodium Tallow Soap | 47.00 |
| Sodium Coconut Soap | 31.00 |
| Coconut Fatty Acid | 7.00 |
| Fragrance | 1.50 |
| Sodium Chloride | 1.10 |
| Titanium Dioxide | 0.25 |
| Trichlorocarban | 0.55 |
| Polyethylene Particles | 2.00 |

Using conventional bar soap making techniques, the above ingredients are mixed together and extruded and cut into soap bars.

The resulting soap bars exhibit low skin abrasion and are useful for cleansing the skin.

Alternatively, the above composition is prepared by replacing the polyethylene particles with particles of equivalent mean particle size or with particles of other mean particle sizes in the range from about 1 micron to about 75 microns, selected from one or more of the following materials: polybutylene, polyisobutylene, polymethylstyrene, polypropylene, polystyrene, polyurethane, nylon, and teflon.

What is claimed is:

1. A nonabrasive personal cleansing composition comprising:

(a) from about 0.05% to about 40% of water insoluble particles selected from the group consisting of polybutylene, polyethylene, polyisobutylene, polymethylstyrene, polypropylene, polystyrene, polyurethane, nylon, teflon, polyhalogenated olefins, polyethylene/polypropylene copolymer, polyethylene/propylene/isobutylene copolymer, polyethylene/styrene copolymer and mixtures thereof having a mean particle size diameter from about 20 microns to about 50 microns, with greater than about 95% of said particles in said composition having a diameter less than about 75 microns, (b) from about 0.05% to about 40% of a surfactant selected from the group consisting of sodium cetearyl sulfate, sodium lauryl sulfate, sodium lauryl sarcosinate, sodium cocoyl isethionate, coamidopropyl betaine, sodium laureth sulfate, cetyl dimethyl betaine, ammonium lauryl sulfate, sodium tallow soap, sodium coconut soap, ceteth-10, steareth-21, steareth-2, ceteth-2, glyceryl stearate, glucose amides, dilauryl dimethyl ammonium chloride, distearyl dimethyl ammonium chloride, dimyristyl dimethyl ammonium chloride, dipalmityl dimethyl ammonium chloride, and mixtures thereof, (c) from 0% to about 50% of an emollient selected from the group consisting of mineral oil, petrolatum, cholesterol, dimethicone, dimethiconol, diisopropyl adipate, isopropyl myristate, myristyl myristate, cetyl ricinoleate, sorbitan distearate, sorbitan dilaurate, sorbitan stearate, sorbitan laurate, sucrose laurate, sucrose dilaurate, sodium isostearyl lactylate, lauryl pidolate, sorbitan stearate, stearyl alcohol, cetyl alcohol, behenyl alcohol, PPG-14 butyl ether, PPG-15 stearyl ether, and mixtures thereof;

(d) from about 20% to about 99.85% water, (e) from about 0.1% to about 10% of a material selected form the group consisting of salicylic acid, lactic acid, glycolic acid, aloe vera, panthenol, pantothenic acid, clove oil, menthol, camphor, eucalyptus oil, eugenol, menthyl lactate, retinol, retinoic acid, azelaic acid, witch hazel distillate, allantoin, bisabolol, and mixtures thereof.

2. A composition according to claim 1 which further comprises from about 0.1% to about 10% of a skin conditioner selected from the group consisting of glycerin, urea, propoxylated glycerol, and mixtures thereof.

* * * * *

UNITED STATES PATENT AND TRADEMARK OFFICE
CERTIFICATE OF CORRECTION

PATENT NO.    : 5,720,961
DATED         : February 24, 1998
INVENTOR(S)   : Timothy John Fowler et al.

It is certified that error appears in the above-identified patent and that said Letters Patent is hereby corrected as shown below:

At column 2, line 37 "having a is mean" should read --having a mean--.

At column 3, line 29 "25° C.;" should read --25° C.,--.

At column 8, line 3 "group ranging from" should read --group having from--.

At column 8, line 22-23 "$R_1$ alternatively" should read --$R_1$ is alternatively--.

At column 11, line 10 "$R^1$" should read --$R'$--.

At column 12, line 40 "C1-$C_3$" should read --$C_1$-$C_3$-- at both occurrences.

At column 15, line 18 "Amnmonium" should read --Ammonium--.

At column 18, line 33 "particie" should read --particle--.

Signed and Sealed this

Fourteenth Day of July, 1998

Attest:

BRUCE LEHMAN

*Attesting Officer*     *Commissioner of Patents and Trademarks*